(12) United States Patent  
Gupta et al.

(10) Patent No.: US 10,357,621 B2  
(45) Date of Patent: Jul. 23, 2019

(54) LUER CONNECTION ADAPTERS FOR RETRACTABLE NEEDLE SYRINGES

(71) Applicant: UNITRACT SYRINGE PTY LTD, Sydney (AU)

(72) Inventors: Jyoti Gupta, Atlanta, GA (US); Brandon J. McKee, Nesquehoning, PA (US); Daniel A. Heinsbergen, Narbeth, PA (US)

(73) Assignee: Hikma Pharmaceuticals LLC, Amman (JO)

( * ) Notice: Subject to any disclaimer, the term of this patent is extended or adjusted under 35 U.S.C. 154(b) by 147 days.

(21) Appl. No.: 15/354,712

(22) Filed: Nov. 17, 2016

(65) Prior Publication Data

US 2017/0065775 A1    Mar. 9, 2017

Related U.S. Application Data

(63) Continuation of application No. 14/454,172, filed on Aug. 7, 2014, now Pat. No. 9,931,480.

(Continued)

(51) Int. Cl.  
*A61M 5/00* (2006.01)  
*A61M 5/32* (2006.01)  
(Continued)

(52) U.S. Cl.  
CPC ........ *A61M 5/5086* (2013.01); *A61M 5/3134* (2013.01); *A61M 5/3221* (2013.01);  
(Continued)

(58) Field of Classification Search  
CPC .. A61M 2005/3104; A61M 2005/3106; A61M 2005/323; A61M 5/5086  
See application file for complete search history.

(56) References Cited

U.S. PATENT DOCUMENTS 2,656,836 A    10/1953    Hickey et al.  
4,220,151 A    9/1980    Whitney  
(Continued)

FOREIGN PATENT DOCUMENTS

EP    1923086 A1    5/2008  
EP    2015802 A2    1/2009  
(Continued)

OTHER PUBLICATIONS

International Preliminary Report on Patentability dated Jul. 30, 2015, in related International Application No. PCT/US2014/50116, filed Aug. 7, 2014.

(Continued)

*Primary Examiner* — Rebecca E Eisenberg  
(74) *Attorney, Agent, or Firm* — Wiley Rein LLP (57) ABSTRACT

A connector mountable to a syringe barrel has a proximal barrel-engaging portion, a distal luer fitment portion, and a fluid aperture therethrough. The barrel-engaging portion of the connector includes an axial ledge configured to abut the axial distal edge of a glass syringe barrel. The connector facilitates mounting a luer assembly to the barrel. The luer assembly may be a tip cap having a complementary luer fitment for connection to the luer fitment portion of the connector. The luer assembly may be a luer needle assembly having a complementary luer fitment for connection to the luer fitment portion of the connector. The connector and syringe may further include an immobile, compressible needle seal. The needle seal is adjacent to or engageable with the barrel-engaging portion of the connector. The syringe may be configured with a plunger capable of engaging a retractable needle.

13 Claims, 7 Drawing Sheets

Related U.S. Application Data (60) Provisional application No. 61/863,098, filed on Aug. 7, 2013, provisional application No. 61/898,077, filed on Oct. 31, 2013.

(51) Int. Cl.
*A61M 5/31* (2006.01)
*A61M 5/50* (2006.01)
*A61M 5/34* (2006.01)

(52) U.S. Cl.
CPC ........ *A61M 5/3232* (2013.01); *A61M 5/3234* (2013.01); *A61M 5/345* (2013.01); *A61M 5/347* (2013.01); *A61M 2005/3104* (2013.01); *A61M 2005/3106* (2013.01); *A61M 2005/323* (2013.01); *A61M 2005/3231* (2013.01); *A61M 2005/3241* (2013.01)

(56) References Cited

U.S. PATENT DOCUMENTS

| | | |
|---|---|---|
| 4,294,250 A | 10/1981 | Dennehey |
| 4,607,868 A | 8/1986 | Harvey et al. |
| 5,122,117 A | 6/1992 | Haber et al. |
| 5,322,515 A | 6/1994 | Karas et al. |
| 5,533,708 A | 7/1996 | Atkinson et al. |
| 5,555,908 A | 9/1996 | Edwards et al. |
| 5,620,427 A | 4/1997 | Werschmidt et al. |
| 5,624,402 A | 4/1997 | Imbert |
| 5,651,776 A | 7/1997 | Appling et al. |
| 5,807,345 A | 9/1998 | Grabenkort |
| 6,004,299 A | 12/1999 | Arai et al. |
| 6,027,482 A | 2/2000 | Imbert |
| 6,190,364 B1 | 2/2001 | Imbert |
| 6,202,901 B1 * | 3/2001 | Gerber ............... B65D 47/2081 137/859 |
| 6,280,418 B1 | 8/2001 | Reinhard et al. |
| 6,569,118 B2 | 5/2003 | Johnson et al. |
| RE43,597 E | 8/2012 | Johnson et al. |
| 9,302,056 B2 * | 4/2016 | Thorley ............... A61M 5/3234 |
| 2004/0133169 A1* | 7/2004 | Heinz ................. A61M 5/3134 604/187 |
| 2004/0236283 A1 | 11/2004 | Tang |
| 2007/0083157 A1 | 4/2007 | Belley et al. |
| 2011/0046601 A1* | 2/2011 | Smith ................... A61M 5/288 604/506 |
| 2011/0115578 A1 | 5/2011 | Quan et al. |
| 2013/0079716 A1 | 3/2013 | Thorley et al. |
| 2013/0338575 A1 | 12/2013 | Glocker et al. |

FOREIGN PATENT DOCUMENTS

| | | |
|---|---|---|
| WO | WO0174424 | 10/2001 |
| WO | 2011/057335 A1 | 5/2011 |

OTHER PUBLICATIONS

International Search Report and Written Opinion dated Dec. 11, 2014, in related International Application No. PCT/US2014/50116, filed Aug. 7, 2014.

European search report dated Feb. 14, 2017, by EPO in related European patent application No. 14835054.9.

* cited by examiner

LUER CONNECTION ADAPTERS FOR RETRACTABLE NEEDLE SYRINGES

RELATED APPLICATIONS

This application is a continuation of U.S. patent application Ser. No. 14/454,172, filed on Aug. 7, 2014, which claims priority benefit of U.S. provisional applications Ser. No. 61/863,098, filed 7 Aug. 2013 and No. 61/898,077, filed 31 Oct. 2013. The contents of these applications are hereby incorporated by reference in their entireties for all purposes.

FIELD

The embodiments described herein relate to syringes. More particularly, the embodiments provide for connectors configured to connect to syringe barrels and provide a luer fitment capable of connecting to selectable retractable needle attachments for delivery of fluids.

BACKGROUND

Today's healthcare practitioners are usually provided with medical devices that are ready to use, because the devices are sterilized during manufacture. This is particularly true of syringes that are used to administer parenteral drugs and other medical solutions. A syringe typically includes a plastic barrel having a substantially closed end and an opposite open end. The open end is sealed by a slidable piston plunger. The closed end of the syringe has a dispensing port communicating with a male luer fitment, for dispensing the contents of the syringe. The syringe, as manufactured, may be prefilled with a liquid, part-filled with a lyophilized powder, or empty, for example. A removable end cover, such as a luer cap is placed over the luer fitment during manufacture so as to seal the contents within the barrel. Prefilled syringes are advantageous in avoiding confusion whether a vial is multidose or single dose, or confusion regarding which diluent should be used with a given lyophilized or powder medicament, and may provide a suitable housing for storage and shipping of sensitive pharmaceuticals such as biologics. Furthermore, use of prefilled syringes, particularly those with safety mechanisms, limits health professionals exposure to used syringes, inadvertent needlestick injuries, and possible exposure to infective pathogens or other contaminants.

Because of the increasing demand for prefilled syringes, there is a proportional increasing need syringes that are made or materials resilient to degradation or interaction with the pharmaceutical or other agent held within the syringe. Additionally, there are filled-on-demand substances that are not compatible with existing plastic syringes. In an attempt to overcome these issues, many syringe manufacturers have returned to the manufacture of glass syringes or syringes in which at least the barrel is glass. Current commercial versions of glass syringes have glass tips that are housed within plastic adapter structures for connection to syringes or other delivery means. These glass syringes have several disadvantages: the tips are fragile and may break during preparation or use, leading to potentially dangerous sharps; the syringes leak around imperfect seals between the glass and the adapter; plastic adapter structures may spontaneously disconnect from the glass tip; or the tips may clog due to the narrow nature of the configured glass tips.

Further, in developing syringes with luer connections, relatively complicated luer assemblies have been devised that are often adapted for a particular syringe barrel shape or configuration and cannot be readily mounted to a syringe barrel having a different shape or configuration. This is particularly a problem with glass syringe barrels which are generally in short supply, many of which glass barrels do not have a desired shape or configuration for mounting a luer assembly. Alternatively, the syringes may be manufactured with a pre-formed luer assembly, but this adds substantial complexity and cost to the process for manufacture of such syringes. Therefore, there is increasing demand for resilient syringes with adequate luer connection adapters.

Additionally, the practice of sharing syringes without adequate sterilization between successive users is a major contributor to the transfer of Human Immunodeficiency Virus and Hepatitis with subsequent severe repercussions for the sufferer and at a high cost to society for supporting and providing medical attention to sufferers. In response to this problem, syringes have been developed with the aim of preventing syringe re-use. One solution has been to develop syringes where the needle is permanently retractable into the barrel of the syringe, in which retraction may be driven by a compressed spring. Generally, spring decompression is relatively uncontrolled such that, in use, the excessively forceful needle retraction can result in blood splattering when air is forced from the syringe barrel as the needle retracts into the barrel. Therefore, there is a need for more "user friendly" retractable syringes that do not compromise the safety features provided by the syringe.

SUMMARY

The embodiments of the present invention provide for syringe distal connectors that facilitate mounting of a luer assembly to pre-formed resilient syringe barrel, such as, for example, a straight, glass barrel, and syringes including these connectors and further comprising a retractable needle assembly. The embodiments herein provide for a distal connector that is easily adaptable to a variety of syringe barrels for retractable needles and obviates the need to have a particular barrel shape or configuration for mounting a luer assembly thereto. Aspects of these embodiments provide for a relatively simplified luer assembly that comprises fewer or simpler components, thereby providing a user-friendly and safe syringe while keeping manufacturing costs to a minimum, or facilitating mass distribution of syringes. For example, the embodiments of the present invention permit the use of straight glass barrels rather than glass barrels with formed distal tips, which are significantly more costly to manufacture. Other embodiments provide efficient delivery of fluid contents, thereby minimizing waste of fluid contents.

In a one aspect, the embodiments provide a distal connector configured to couple with, mount to, or engage with, a syringe barrel, the connector comprising a body that includes a barrel-engaging portion, a distal portion configured to engage a luer fitment or selectable retraction needle, and an aperture disposed centrally and axially through the connector, in which the syringe barrel further comprises an assembly for retractable needle syringes. As used in reference to the present embodiments, "adapter," "luer connection adapter," "lure connection" may be used interchangeably with "connector." The connector is also configured to couple or mount to, or engage with, a needle assembly. The connector further comprises an aperture disposed centrally and axial within the connector, that may serve as a needle aperture. In at least one embodiment, the connector (e.g., a luer connection adapter) also includes a needle seal that may be mounted within the barrel, for example, adjacent and proximal to the barrel-engaging portion of the connector, and further comprising an aperture positioned to communicate with the connector. In use, the needle seal may be compressible but substantially immobile. In a particular embodiment, the needle seal is engaged with a portion of the connector. Suitably, when the connector is coupled with a needle assembly, a cannula of the needle assembly is received or accommodated by, or extends through, the needle aperture of the connector.

Another embodiment provides for a syringe barrel comprising a retractable needle, the connector and, optionally, the needle seal. Another embodiment provides for a syringe comprising the connector situated in a syringe barrel, optionally with the needle seal, the retractable needle assembly, and a plunger.

An aspect of the embodiments provides a method of assembling all or part of a syringe comprising the novel connector and retractable syringe. A further aspect provides a method of use of the syringe, including the step of delivering fluid contents of the syringe to a subject, such as a human. The syringe of the aforementioned aspects may be a syringe for connection, via luer lock connection, to needle assembly. A luer lock connection can be a conical or tapered connection having a screw-threaded mating configuration. The syringe can be a pre-filled syringe, a mixing syringe, a sequential delivery syringe, or the like.

At least one embodiment provides for a retractable syringe that comprises a mechanism to facilitate needle retraction in a controlled or regulated manner, which mechanism is housed in the plunger of a syringe.

BRIEF DESCRIPTION OF THE DRAWINGS

Non-limiting embodiments of the invention are described herein with reference to the following drawings wherein.

DETAILED DESCRIPTION

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless clearly indicated otherwise by context. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims. The terms male and female may be used interchangeably to describe corresponding components or complementary aspects thereof and are not a limitation to either particular structure unless context clearly indicates otherwise.

As used herein to describe the relative positions of the components of the present embodiments, the terms "axial" or "axially" refer generally to a longitudinal axis "A" of the barrel of a syringe and plunger in which or around components are positioned, although not necessarily symmetrically there-around. The term "radial" refers generally to a direction perpendicular to axis A. The terms "proximal," "rear," "rearward," "back," or "backward" refer generally to an axial direction in the direction "P." The terms "distal," "front," "frontward," "depressed," or "forward" refer generally to an axial direction in the direction "D," toward the dispensing end of the syringe.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes.

As used herein, the term "glass" should be understood to include other similarly non-reactive materials suitable for use in a pharmaceutical grade application that would normally require glass (e.g., Type I borosilicate glass), including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, the term "plastic" can include pharmaceutical grade non-reactive polymers or elastomers that are approved for use in applications where they are in direct contact with therapeutic substances, such that the plastics do not interact with the substances contacting the plastic and are not readily susceptible to leaching or gas migration under ambient temperature and pressure.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure. It is appreciated in the art that particular elastomeric polymers are better suited for contact with pharmaceuticals than are some particular plastics, hence the elastomeric material can be a biocompatible material. As used herein, the term "elastomer," "elastomeric" or "elastomeric material" may also include other biocompatible materials, such as styrenic block copolymers (TPE-s), polyolefin blends (TPE-o), elastomeric alloys (TPE-v or TPV), thermoplastic polyurethanes (TPU), thermoplastic copolyesters, and/or thermoplastic polyamides, among other biocompatible materials which are approved for use with pharmaceutical grade substances, and are not readily susceptible to leaching or gas migration under ambient temperature and pressure.

References to "prefillable" generally refer to syringes comprising components for filling with a substance prior to dispensing the substance for its intended use. More specifically, in the context of the syringe embodiments, the term "prefillable" refers to a configuration or state in which a substance may be introduced into the syringe any time prior to the dispensing by the syringe of the substance(s) for their intended use (such as delivery into a subject or device either directly or indirectly). A prefillable syringe thus includes syringes described herein as prefilled, fill-at-time-of-use, fill-on-demand, ready-to-use, and the like.

References to "pharmaceutical agent," "pharmaceutically active," "pharmaceutical," "drug," "medicament" "active agent," "active drug" and the like, refer in a general sense to substances useful in the medical and scientific arts as suitable for delivery via a syringe, including, for example, drugs, biologics, diagnostic agents (e.g., dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics.

At least one embodiment provides for a connector comprising a distal portion configured to engage a luer fitment, a proximal syringe barrel-engaging portion comprising a circumferentially disposed ledge configured to abut an axial distal edge of a glass syringe barrel, and a fluid aperture axially therethrough, wherein the syringe is configured with, or configured to receive, a retractable needle assembly.

At least one embodiment provides for syringe assembly comprising a glass barrel and a distal connector that includes a distal portion configured to engage a luer fitment, a proximal syringe barrel-engaging portion with an axial ledge configured to abut the axial distal edge of the glass barrel, and a fluid aperture therethrough; wherein the syringe barrel is configured to include or receive a retractable needle assembly. In some embodiments, the connector includes locking means that permanently connect the connector to a connection, such as a needle assembly. Some embodiments of the syringe assembly include a needle seal, located proximal to the connector and having a fluid aperture therethrough, in which the needle seal fluid aperture is configured to align with the connector fluid aperture to form a fluid passage. The needle seal can be constructed of an elastomeric material or a biocompatible material. The needle seal and connector may further include means for fixedly engaging with each other. Some embodiments of the syringe further include a tip cap having a body comprising a projection configured to engage the distal end of the connector fluid aperture and block fluid passage. In particular embodiments, the projection extends through the connector at least into the needle seal. The projection can be constructed of an elastomeric material or a biocompatible material. The projection can be contiguous with or a separate piece of the tip cap. The needle seal and the tip cap ensure that the drug fluid does not contact a non-biocompatible material during transportation and storage, i.e., prior to use. In some embodiments, the distal end of the connector includes a means for irreversibly indicating the tampering with the connector, tip cap, or needle assembly. In some embodiments, the syringe includes a means for irreversibly indicating the tampering with, or use of, the needle assembly.

At least one embodiment provides for a syringe comprising a glass barrel, a plunger, and a distal connector comprising a distal portion configured to engage a luer fitment; a proximal syringe barrel-engaging portion comprising an axial ledge configured to abut the axial distal edge of the glass barrel; and a fluid aperture therethrough. In some embodiments, this syringe further includes a needle seal, located proximal to the connector and having a fluid aperture therethrough, in which the needle seal fluid aperture is configured to align with the connector fluid aperture to form a fluid passage. Some embodiments of the syringe further include a tip cap having a body comprising a projection configured to engage the distal end of the connector fluid aperture and block fluid passage. The needle seal or the projection can be constructed of an elastomeric material. In some embodiments, the plunger includes a means for irreversibly indicating the tampering with, or use of, the plunger. In some embodiments, the tip cap includes a means for irreversibly indicating the tampering with, or removal of, the tip cap.

Another aspect of the present embodiments provides for prefilled syringes comprising a connector and a needle retraction mechanism, in which the syringe is prefilled or prefillable with a substance. The substance can be a pharmaceutical agent. As noted, pharmaceutical agents include, in a general sense, substances useful in the medical and scientific arts as suitable for delivery via a syringe, including, for example, drugs, biologics, diagnostic agents (e.g., dyes or contrast agents) or other substances used for therapeutic, diagnostic, or preventative (e.g., vaccines), or research purposes. For example, the pharmaceutical agent can be a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, or a combination of any of these. Substances that are inactive, but still relevant to medical and scientific arts as suitable for delivery via a syringe, include carriers, excipients, diluents, and the like; as well as substances having beneficial function, such as, for example, adjuvants, isotonic or buffering agents. These active or inactive substances may also include substances having immediate, delayed or sustained release characteristics.

Another aspect of the present embodiments provides for prefilled syringes comprising a connector and retractable needle assembly, in which the syringe is prefilled or prefillable with a substance. The substance can be a pharmaceutical agent, such as, for example, Aciclovir, Amikacin, Amiodarone, Amoxicillin clavulanic acid, Atracurium besylate, Atropine, Azithromycin, Benzatropine mesylate, Bupivacaine, Butorphanol tartrate, Calcium Folinate, Carboplatin, Cefazolin, Cefepime, Cefotaxime Sodium, Cefoxitin sodium, Ceftriaxone sodium, Cefuroxime sodium, Chlorphenamine Maleate, Ciprofloxacin, Clindamycin phosphate, Deferoxamine Mesylate, Dexamethasone Sodium Phosphate, Diazepam, Diclofenac Sodium, Enalaprilat, Epinephrine, Epirubicin HC1, Esmolol, Fluconazole, Flumazenil, Fosphenytoin Sodium, Furosemide, Gemcitabine, Gentamicin sulphate, Granisetron, Hydrocortisone Hemisuccinate, Hyoscine Butylbromide, Irinotecan, Ketamine, Lidocaine Hydrochloride, Lincomycin, Methohexital Sodium, Methylprednisolone, Metoclopramide Hydrochloride, Metoprolol tartrate, Midazolam HC1, Milrinone, Naloxone HC1, Ondansetron, Pamidronic acid, Pancuronium Bromide, Paracetamol, Phenytoin, Piroxicam, Progesterone, Promethazine, Propranolol, Ranitidine, Sodium Valproate, Somatostatin, Teicoplanin, Terbutaline Sulfate, Tramadol Hydrochloride, Vancomycin Hydrochloride, Vecuronium Bromide, Vinorelbine, Water for Injection, Zoledronic Acid, or a mixture of any of these, optionally including additional pharmaceutically acceptable excipients as known in the art.

Figure 1A:
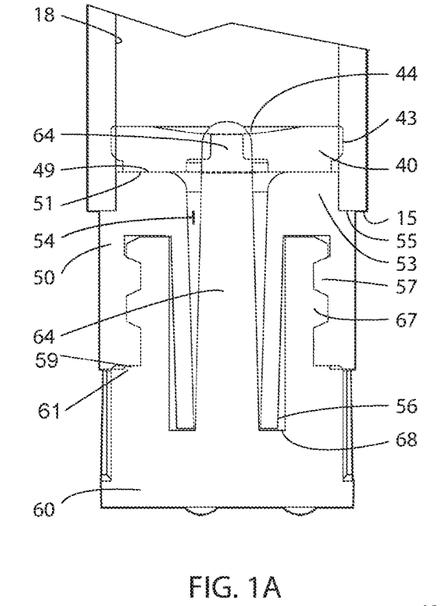
FIG. 1A is a sectional view of an embodiment of a connector assembly and a removable tip cap.
Figure 1B:
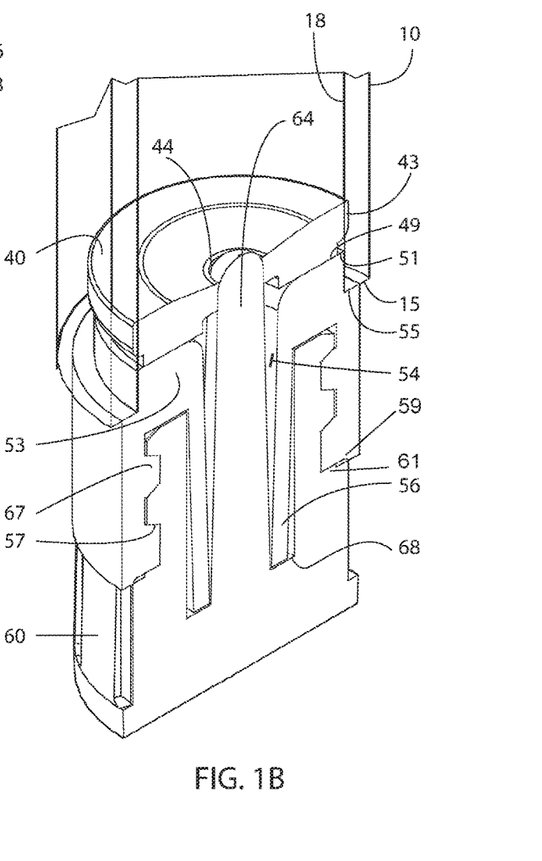
FIG. 1B is an isometric sectional view the embodiment of FIG. 1A.

Referring to FIG. 1, this figure shows an embodiment of a connector comprising a distal portion configured to engage a luer fitment and a proximal syringe barrel-engaging portion, which connector includes a fluid aperture axially therethrough. More specifically, luer connection adapter 50 disposed at the distal end of barrel 10 having a distal connection end 15 and interior wall 18. As shown in FIG. 1, barrel 10 is substantially cylindrical in shape, but the connectors described herein can be adapted for a variety of barrel shapes. The barrel can be formed of glass, but other resilient plastics or polymers may be used in manufacturing the barrel. As shown in FIG. 1, at distal connection end 15 of barrel 10 is mounted barrel luer connector 50. Connector 50 includes an axial ledge or shelf structure 55 configured to abut the distal barrel end 15, thus creating a connection point at which the abutting surfaces can be glued or otherwise permanently affixed to each other. For example, adhesive can be used to permanently connect the barrel and the adapter materials, such as glass and plastic, respectively. The adhesive is typically stable under sterilization and procedures, and storage and use conditions. The adhesive may be a curable adhesive, such as a heat-, time-, water- or UV-light-cured adhesive. The adhesive may be clear or colorless. Such adhesives are well known in the art. Alternatively, a connector can be pressure-connected into the barrel, for example by a design of portion of the adapter that sits within the barrel, such as 53, configured to press outwardly and immobily against the interior surface 18 of barrel 10. Barrel 10 further comprises inside wall 18 which, together with needle seal 40 and typical proximal syringe components such as a plunger, defines fluid space 12 inside barrel 10.

Figure 2A:
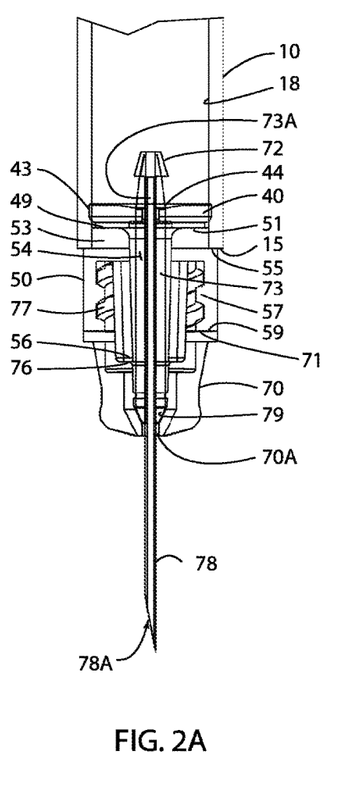
FIG. 2A is a sectional view of an embodiment of a connector having a needle assembly attached thereto.
Figure 2B:
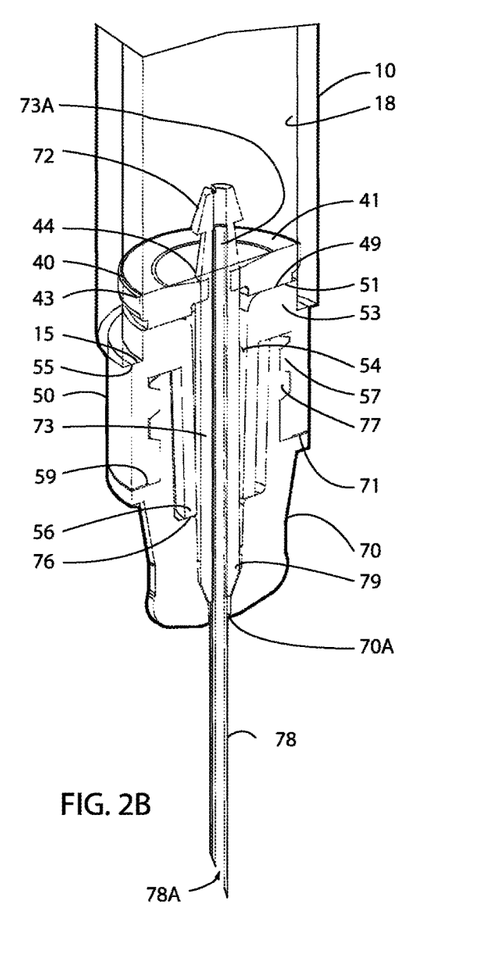
FIG. 2B is an isometric sectional view of the embodiment of FIG. 2A

With further reference to FIG. 1 and FIG. 2, connector 50 includes a luer connection portion comprising a distal luer lock connection having a tapered/conical aspect 56 and a screw-threaded mating structure 57. Connector 50 includes luer fitment 56 that extends distally from the end of syringe barrel 10. Luer fitment 56 is generally tubular and formed with a central, axial bore or fluid passageway extending axially there-through. The outside surface of the male luer fitment is tapered along the extending length to provide a surface sealingly mateable with the inner tapered surface of a female luer connector, thereby establishing a seat for and seal with a female luer hub. Luer adapter 50 further includes screw-thread 57 for further connecting to a luer connection, needle assembly, or other structure. For example, the female luer connector may be in the hub of a sharp needle assembly shown in FIG. 2. Notably, adapter 50 has a center bore or central fluid passageway 54, which may be dimensioned to meet the necessary or desired requirements of the particular fluid or delivery mechanism.

Additionally, as shown in FIG. 1 and FIG. 2, the connector and barrel may further comprise an immobile, compressible elastomeric needle seal 40. The elastomeric needle seal is proximally adjacent to or engageable with the barrel-engaging portion of the adapter. More specifically, in the embodiments of FIG. 1 and FIG. 2, needle seal 40 sits within barrel 10 against interior wall 18, and proximal surface 51 of connector 50 meets distal surface 49 of elastomeric needle seal 40. Needle seal 40 is configured with at least one radial, circumferential ring or rib 43 that bears against barrel interior wall 18 to form a liquid-tight seal. Needle seal 40 further comprises passage 44, configured to align with connector aperture 54. Needle seal 40 can be made of an elastomeric, rubber-based polymer that is particularly resilient to degradation or interaction with chemicals, pharmaceuticals or liquids in general, or may include such materials at proximal surface 41. In at least one embodiment, use of the elastomeric material of the needle seal is more desirable for contact with the contents of a syringe, particularly in prefillable syringes storage conditions, than are typical plastics used for syringes or molded syringe parts.

In the embodiment depicted in FIG. 1, connector 50 includes luer connection portion 57 and barrel-interior portion 53, a barrel-engaging portion 55 and aperture 54 therethrough. The connector shelf or ledge 55 facilitates mounting the connector to distal barrel end 15. As shown in FIG. 1, the connector assembly may include tip cap 60 with proximal surface 61 that abuts distal surface 59 of connector 50; which tip cap includes a female luer fitment 68 for receiving male luer fitment 56, and screw thread 67 complementary to screw thread 57 of the distal luer fitment portion of connector 50. Tip cap 60 further includes elastomeric stem 64 that passes through channel 54 and needle seal channel 44. Stem 64 can be made integral to tip cap 60, or can be a separate component of the tip cap (see FIG. 3). In the configuration shown in FIG. 1, when the tip cap is in place, the contents of a prefilled syringe do not contact the plastic of the syringe connector (the luer connection adaptor) during storage. Instead, such contents contact only the elastomeric materials of needle seal 40 and the proximal end of stem 64. Tip cap 60 can be placed on luer connection adapter 50 before sterilization processes or under aseptic conditions such that it maintains sterility of the luer connector and syringe contents. This is particularly advantageous for use in prefilled syringes.

As shown in FIG. 2, a selectable needle assembly may be utilized and connected to the syringe to facilitate delivery to a user via injection. The needle assembly can be any appropriate needle or needle assembly, without limitation, such as, for example, a retractable needle assembly. In the embodiment of FIG. 2, connector 50 may houses a luer needle assembly having needle hub 70, wherein proximal end 71 of needle hub 70 abuts distal end 59 of the luer connection portion of connector 50. Needle hub 70 houses a first luer fitment 76 and screw thread 77 for connection to a corresponding luer fitment 56 and complementary screw thread 57 of connector 50. Needle 78 is held in channel 73A of needle-over-mold 73, the distal end of the needle-over-mold 79 is held in channel 70A of needle hub 70. In the embodiment of FIG. 2, needle-over-mold 73 has proximal end 72, through which passes channel 73A. In this fashion, fluid communication is possible between and through the interior chamber 12 of barrel 10 and fluid channel 78A of needle 78. A variety of retractable needle assemblies are compatible with the luer connection adapters described herein, such as, for example, needle assemblies described in U.S. Pat. No. 8,167,837.

Figures 3A, 3B:
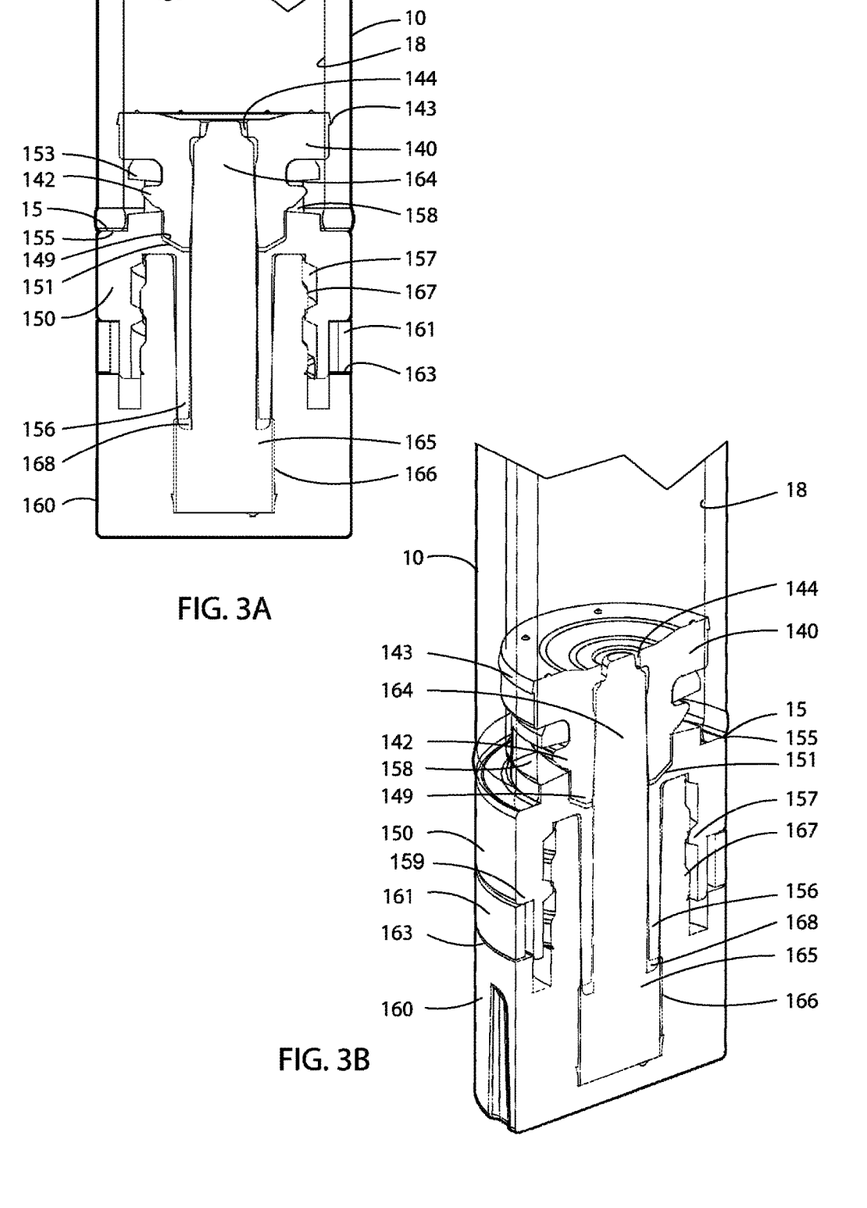
FIG. 3A is a sectional view of an alternative embodiment of a connector assembly and a removable tip cap.
FIG. 3B is an isometric sectional view of the same embodiment.
Figure 3C:
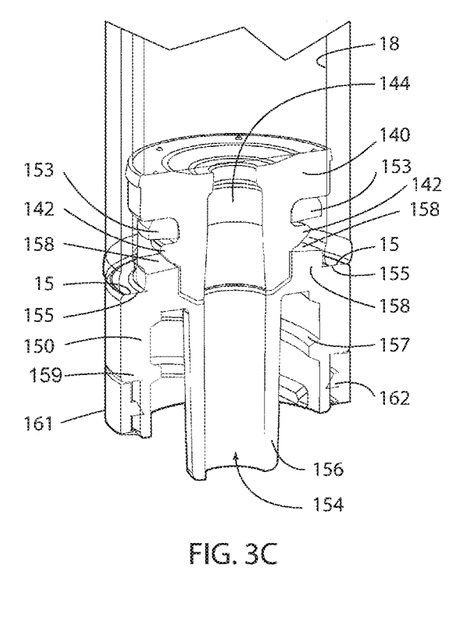
FIG. 3C is an isometric sectional view of the embodiment of FIG. 3A showing the tip cap removed.
Figure 3D:
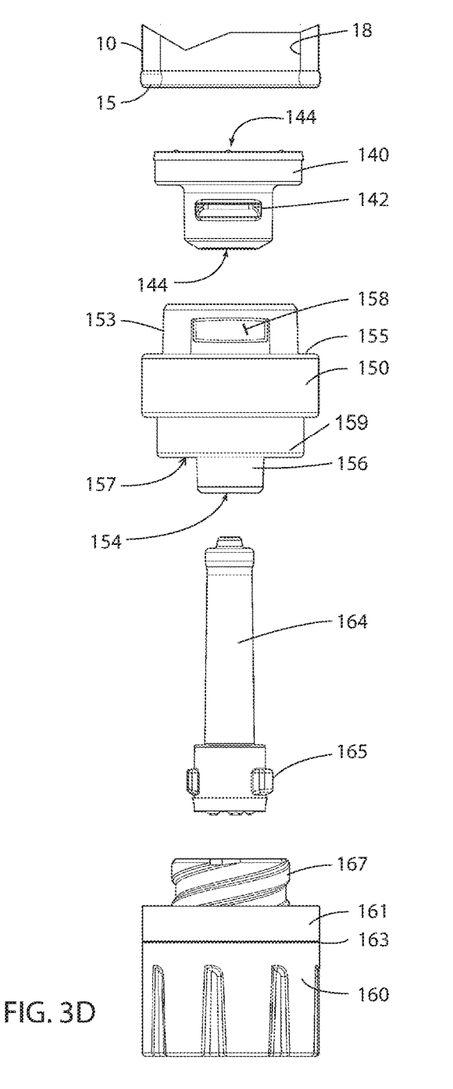
FIG. 3D is a side view of the separate components of the embodiment of FIG. 3A.

Another embodiment of a connector as housed in a syringe includes a distal means for irreversibly indicating the tampering with, or use of, the connector. More specifically, for example, FIG. 3 shows connector 150 includes ledge 155, which abuts and is adhered to distal barrel connection point 15. A proximal portion 153 of connector 150 extends into barrel 10. Connector 150 also includes luer fitment 156 and a thread-screw configuration 157 for attachment to a tip cap, needle assembly, and the like. In this embodiment, needle seal 140 is positioned within barrel 10, abutting its interior 18 and held in place by pressure exerted against surface 18 by ribs 143 or by interaction between protrusion 142 and window 158. Needle seal 140 further includes a locking means comprising protrusion or nub 142 configured to insert into or through an opening or window 158 in adapter 150, such that protrusion 142 and window 158 lock needle seal 140 and connector 150 in an engaged position. Needle seal 140 includes aperture 144, and distal end 149 having a surface that extends axially and distally within the proximal end of connector 150, received by complementary surface 151.

The embodiment of FIG. 3 further comprises tamper-evident tip cap 160. Tip cap 160 includes proximal portion 161 that abuts distal portion 159 of connector 150; which tip cap includes a female luer fitment 168 for receiving male luer fitment 156, and screw thread 167 complementary to screw thread 157 of the distal luer fitment portion of connector 150. Scored line 163 extends circumferentially around and partially, but not fully, through tip cap 160 distal to proximal portion 161, such that attempting to remove the cap provides biofeedback in the form of tangible resistance in attempting to remove the cap, a feeling of quick release when score line 163 is broken fully, and a slight noise like a snap or pop when score line 163 breaks and separates proximal portion 161 from the remainder of the cap structure. Therefore, if an operator finds that tip cap 160 is removed easily without resistance or noise, the operator may assume that the tip cap has been breached, and the device should not be used without consideration that the syringe contents may have been contaminated. Additionally, as shown in FIG. 3C, proximal portion 161 remains attached to connector 150, such as by tooth 162, even after the distal portion of cap 160 has been removed; providing visual feedback that the syringe may have been compromised if not used. In the embodiment of FIG. 3, tip cap 160 is made of resilient plastic to facilitate the tamper-evident features, and thus stem 164 is a separate elastomeric, drug-compatible stem that is seated in and held in place by tip cap cavity 166. Stem 164 may further comprise protrusions 165, shown particularly in FIG. 3D, to secure stem 164 within tip cap 160. Alternative mechanisms can be adapted for use with the connectors in relation to tamper-resistant devices, but in certain embodiments may lack the biofeedback (tactile) associated with breaking of tamper-resistant or tamper-evident seals.

Figure 4A:
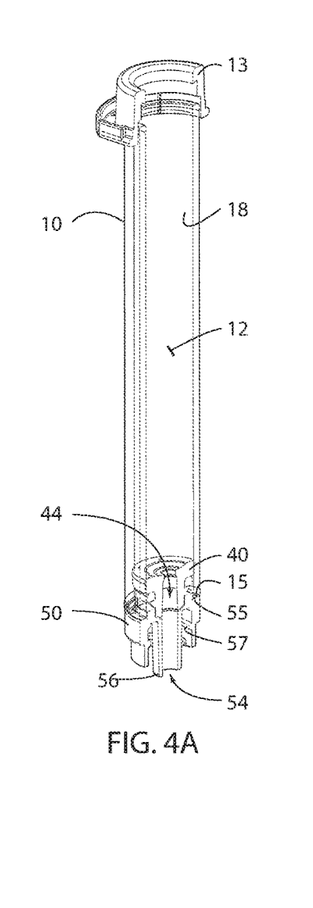
FIG. 4A is an isometric sectional view of an embodiment showing a connector housed in a syringe barrel comprising a collar.
Figure 4B:
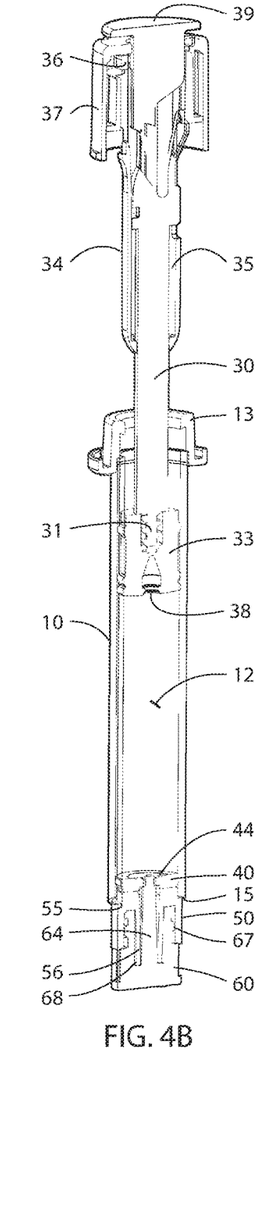
FIG. 4B is an isometric sectional view of an embodiment showing a plunger rod assembly inserted into the syringe barrel.
Figure 4C:
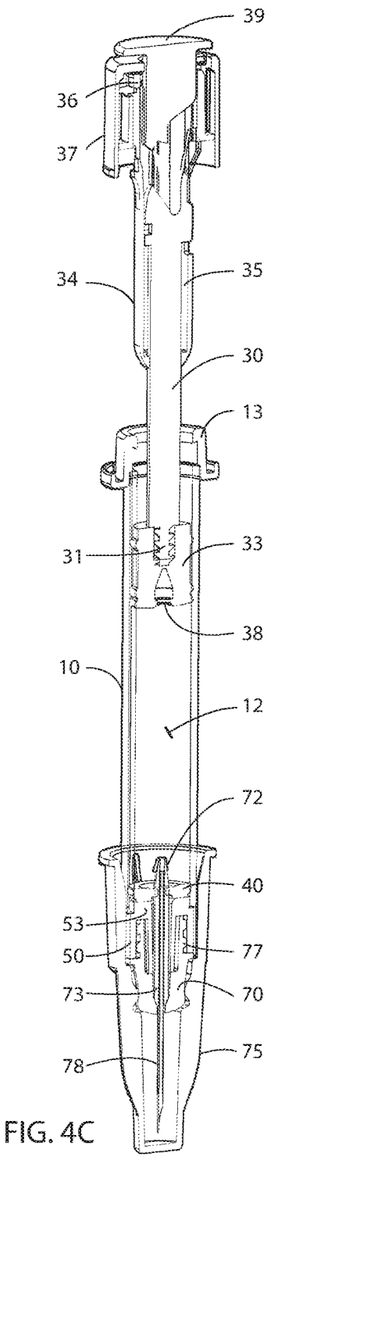
FIG. 4C is an isometric sectional view showing the embodiment of FIG. 4B in which the tip cap of the syringe has been replaced with a needle assembly.

FIG. 4A to FIG. 4C exemplify syringes that include some embodiments of connectors described herein. FIG. 4A shows a syringe assembly comprising a glass barrel; and a distal connector comprising a distal portion configured to engage a luer fitment and a proximal syringe barrel-engaging portion comprising an axial ledge configured to abut the axial distal edge of the glass barrel, and having a fluid aperture therethrough. More specifically, FIG. 4A shows a syringe that has barrel 10 with cap/collar 13, in which interior wall 18 is suitable for contact with a substance housed in void 12. The embodiment of FIG. 4A further includes needle seal 40, having aperture 44 in fluid communication with aperture 54 of connector 50. Connector 50 further includes male luer fitment 56 and screw-threads 57 for connection to a needleless access device (such as an intravenous line), or a needle assembly, and the like. Connector 50 is connected at ledge 55 to the distal connection end 15 of barrel 10.

At least one embodiment of the present invention relates to a syringe comprising a glass barrel; a plunger; and a distal connector comprising a distal portion configured to engage a luer fitment, a proximal syringe barrel-engaging portion comprising an axial ledge configured to abut the axial distal edge of the glass barrel, and having a fluid aperture therethrough. Syringes comprising plungers can include, for example, standard plungers known in the art instead of the plunger assembly shown in FIG. 4B and FIG. 4C. The syringe can further include a needle seal, located proximal to the connector, having a fluid aperture therethrough, wherein the needle seal fluid aperture is configured to align with the connector fluid aperture to form a fluid passage.

FIG. 4B and FIG. 4C depict syringes outfitted with a retractable plunger configuration. The plunger assembly includes plunger rod 30, attached to plunger seal 33 by complementary screw-threads 31. Plunger seal 33 further houses cavity 38, configured to connect with connector 72 on the proximal end of needle-over-mold 73. Plunger rod 30 comprises on it proximal end an interface 39 which can be used to depress the plunger rod assembly. Plunger rod 30 further includes outer plunger 34, and the void 35 between rod 30 and outer rod 34 houses biasing means. Plunger rod 30 further includes plunger cap 37 and plunger clip 36. As shown in FIG. 4B, the syringe may be capped at the distal end by a tip cap. As described herein, an elastomeric tip cap, for example, may be used for this purpose though plastic tip caps and tip caps of other materials may also be utilized. If the syringe is to be utilized with a needle assembly, a needle assembly may be contained in a needle cap. FIG. 4C shows a syringe with the needle assembly connected via the connector 50. A needle cap, such as needle cap 75, containing the needle assembly may be utilized to safely connect the needle assembly to the syringe (i.e., without exposure to the needle).

The embodiments of the present invention may further utilize additional components to enhance the use of the syringe, such as tamper-resistant or tamper-evident aspects to prevent or evidence tampering with the syringe. These tamper-resistant or tamper-evident aspects may deter or prevent an unauthorized user from, for example, removing the plunger rod, or tip cap, or provide evidence of tampering such that an unauthorized user will be discouraged from compromising the syringe. These tamper-resistance aspects could be located along the plunger rod, plunger seal, or the barrel flange, collar/cap, release ring, or needle cap. These tamper-resistance aspects could be axially positioned or longitudinally oriented, or in a number of other known configurations. The tamper-resistance aspects may additionally or alternatively be located on the plunger rod. Alternative mechanisms can be adapted for use with the connectors in relation to tamper-resistant devices; these mechanisms may be identical or similar to tamper-resistant devices described herein, but in certain embodiments may lack the biofeedback (tactile) associated with breaking of tamper-resistant or tamper-evident seals.

At least one embodiment of the present invention provides for a syringe comprising a glass barrel; a plunger; a distal connector comprising a distal portion configured to engage a luer fitment, a proximal syringe barrel-engaging portion comprising an axial ledge configured to abut the axial distal edge of the glass barrel, and a fluid aperture therethrough; a needle seal located proximal to the connector and having a fluid aperture therethrough, wherein the needle seal fluid aperture is configured to align with the connector fluid aperture to form a fluid passage; a retractable needle; wherein the plunger comprises a retractable needle mechanism, such as a plunger member capable of engaging the retractable needle, a plunger housing and a biasing member. These embodiments are advantageous in providing means within the plunger that facilitate a controlled rate of retraction of the retractable needle. By controlling the rate of needle retraction, the likelihood of blood splattering is reduced, thereby improving the user-friendliness and appeal of the retractable syringe. Typically, the syringe is a prefilled syringe. Such devices are exemplified in U.S. Pat. No. 8,167,837.

Figure 5A:
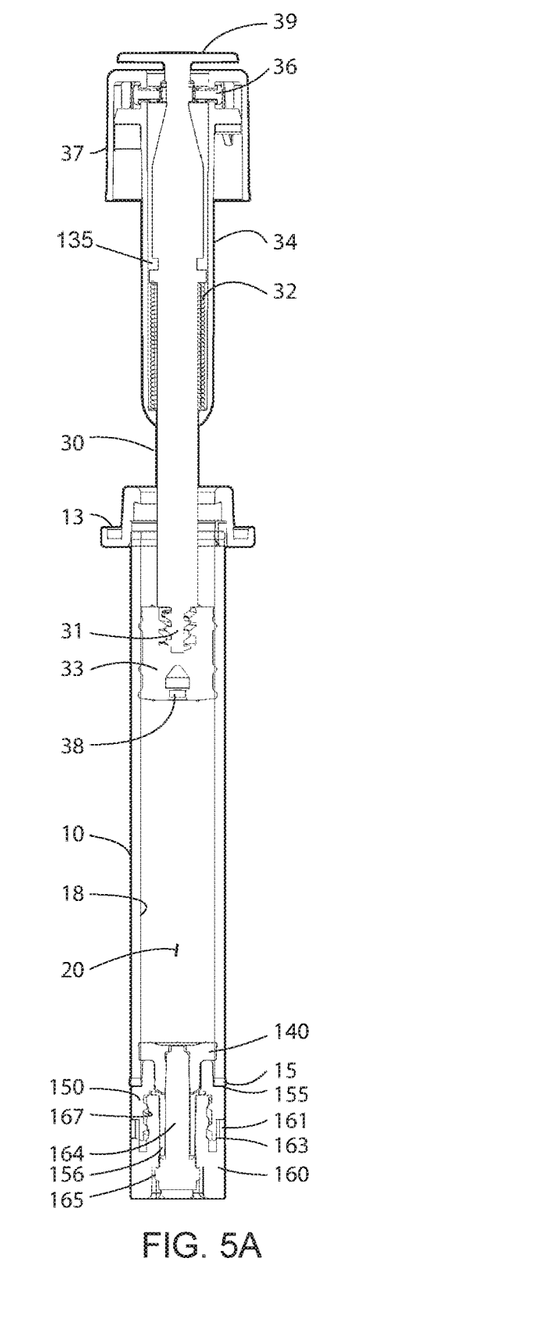
FIG. 5A is a sectional view of a connector assembly in a syringe showing a plunger configured to retract a needle from a retractable needle assembly.
Figure 5B:
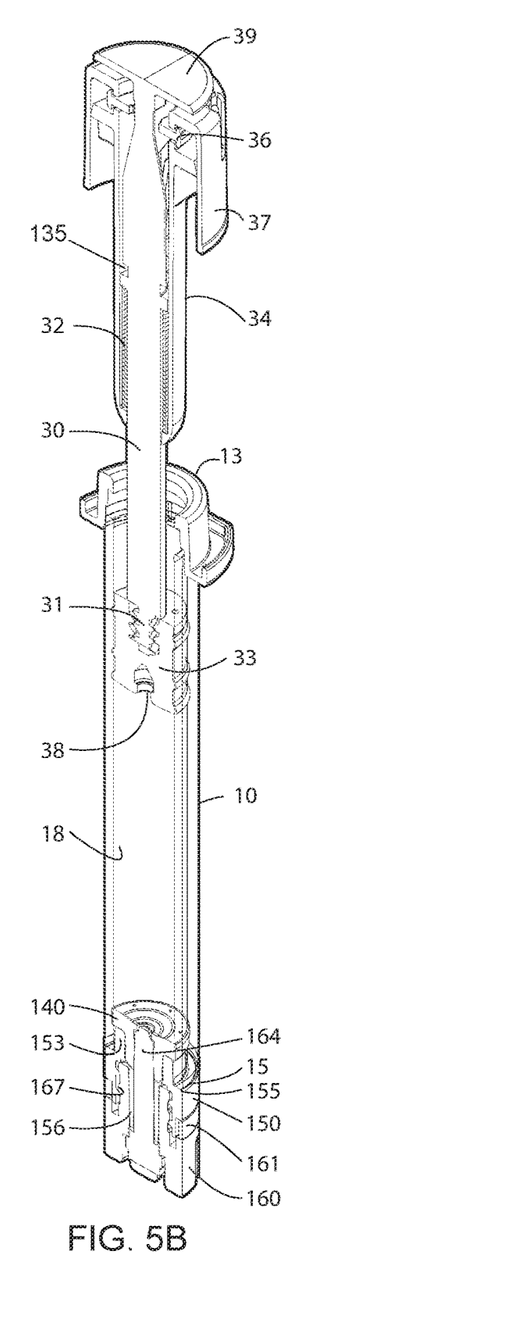
FIG. 5B is an isometric sectional view of the embodiment of FIG. 5A.
Figure 6A:
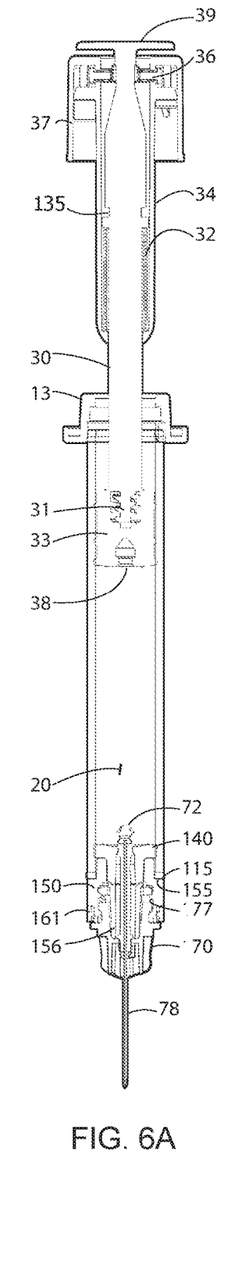
FIG. 6A is a sectional view of an embodiment of a connector assembly and a retractable needle assembly in a pre-delivery position.
Figure 6B:
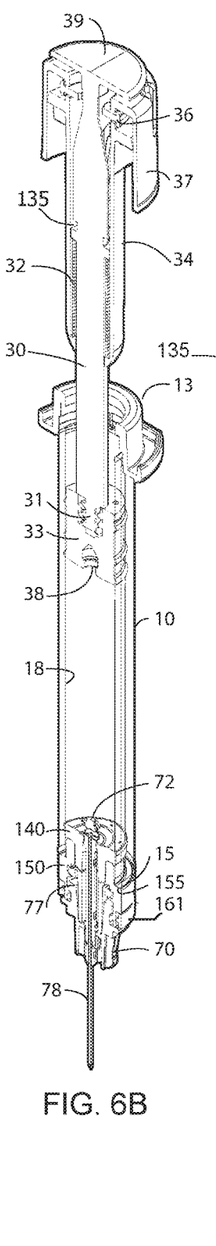
FIG. 6B is an isometric sectional view of the embodiment of FIG. 6A.
Figures 6C, 6D:
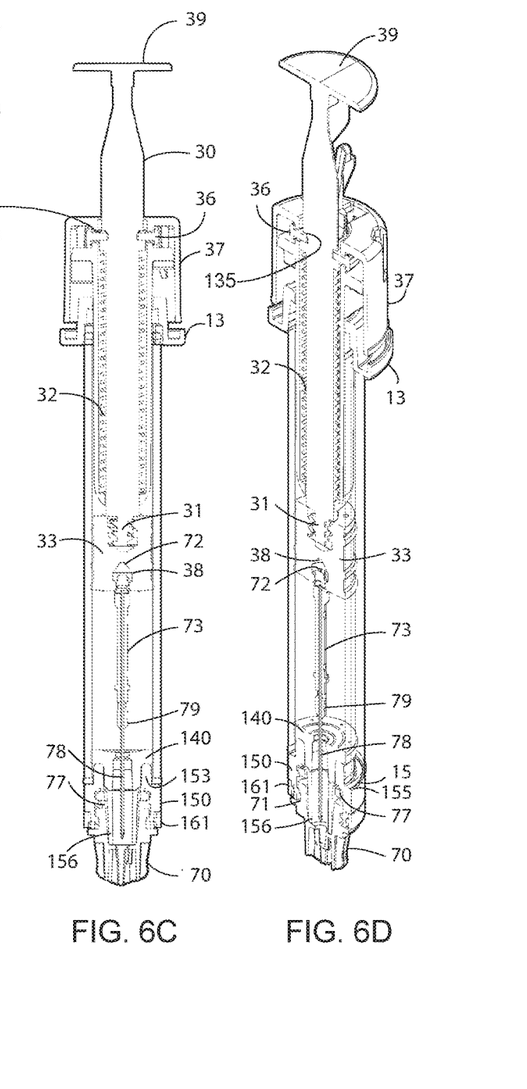
FIG. 6C is a sectional view of the embodiment of FIG. 6A in which the needle has been retracted into the syringe.
FIG. 6D is an isometric sectional view of the syringe embodiment shown in FIG. 6C.

Referring to FIG. 5 and FIG. 6, these figures show an embodiment of a plunger-controlled retractable syringe having a retractable needle assembly. FIG. 5A and FIG. 5B show an embodiment of a retractable needle syringe housing a novel connector, and a needle seal, tip cap, and plunger assembly. More specifically, syringe barrel 10 comprises cap structure 13, interior wall 18, needle seal 140, plunger seal 33, wherein the position of needle seal 140 and plunger seal 33 define chamber 20 in which fluid may be filled or prefilled. Connector 150 connects at ledge 155 to distal end of barrel 15. In FIG. 5, a selectable, retractable needle assembly has not yet been inserted into the connector. Instead, tamper-evident tip cap 160 protects the sterility and integrity of the syringe. Details of the distal connector assembly are further discussed in the context of preceding figures. Plunger seal 33 is connected to plunger rod 30 by complementary screw-threads 31, although other connection means known in the art can be used, such as snap-on attachments, adhesives, or one-piece construction. Plunger seal 33 further includes recess 38, configured to receive and engage with a complementary connector of a needle assembly. Plunger rod 30 extends distally and axially through cap 13 into barrel 10, and extends proximally and axially through plunger cap 37 and clip 36, ending proximally with tab 39 which serves as a user interface for depression of the plunger. Plunger rod 30 and plunger housing 34 also engage biasing member 32, which in this embodiment is a spring surrounding plunger rod 30.

Referring to FIG. 6A and FIG. 6B, these figures show the device of FIG. 5 outfitted with a retractable needle assembly engaged with connector 150 and in position to deliver a substance from chamber 20 through needle 78. More specifically, needle or cannula 78 is secured in needle-over-molding 73, which in turn is reversible engaged in needle hub 70, which needle hub includes luer connector means 77 engaged with luer fitment 156 of connector 150. Needle-over-mold 73 passed through needle seal 140, and further comprises proximal connector 72, configured to irreversible engage with recess 38 in plunger seal 33. Also shown in FIG. 6A and FIG. 6B, biasing member 32 which surrounds plunger rod 30. Note that in FIG. 6, the proximal portion of tip cap 161 is engaged with connector 150, verifying that even if the needle could be removed from connector 150, the syringe has been opened and should be considered "used."

FIGS. 6C and 6D present representations of the syringe when the needle has been retracted into the syringe. More specifically, full depression of seal 33 pushes recess 38 into engagement with proximal end 72 of needle-over-mold 73. Full depression of plunger rod 30 also engages plunger cap 37 with collar 13 and releases plunger rod 30 from engagement with plunger rod housing 34 and plunger cap 34. Full depression of plunger rod 30 also causes biasing member 32 to release, whereby the operator, by slowly releasing distal pressure on interface 39 and allowing plunger rod 30 to move axially, controls the rate at which biasing means 32 decompresses, which thereby draws needle-over-mold 73 and needle 78 into syringe barrel 10 at a rate controllable by the operator. Proximal movement of plunger rod 30 allows clip 36 engagement of plunger rod 30 at clip receiver 135, thereby preventing further movement of plunger rod 30 such that the needle can no longer be extended or removed from the syringe. Additional tamper-resistance aspects can be located on or in the proximal or distal portions of the syringe, such as along the plunger rod, in the plunger seal, barrel, tip hub, or connector of the syringe. These tamper-resistance aspects can be axially positioned or longitudinally oriented, or be adapted for use in a number of other known configurations.

Each of the embodiments described herein may be used alone or in combination with one or more other embodiments in a syringe. Throughout the specification, the aim has been to describe the preferred embodiments of the invention without limiting the invention to any one embodiment or specific collection of features. Various changes and modifications may be made to the embodiments described and illustrated without departing from the present invention.

What is claimed is:
1. A syringe comprising:
a barrel;
a plunger;
a distal connector comprising a fluid aperture, a distal portion configured to engage a lure fitment, and an axial ledge separating the distal connector into the distal portion and a proximal portion configured to engage an interior wall within the distal end of the barrel;
a needle seal, located at least partially proximal to the distal connector, having a fluid aperture therethrough; and
a tip cap engaged with the distal connector, the tip cap comprising a proximal portion abutting the distal portion of the distal connector;
wherein the tip cap is configured to provide evidence of tampering to a user upon removal of the tip cap from the distal connector.

2. The syringe of claim 1, the distal connector further comprising a first threaded portion and the tip cap comprising a second threaded portion which is configured to be complementary to the first threaded portion.

3. The syringe of claim 1, wherein the tip cap is configured such that the proximal portion of the tip cap disengages from the remainder of the tip cap upon removal of the tip cap from the distal connector such that the proximal portion of the tip cap remains attached to the distal connector.

4. The syringe of claim 3, the tip cap further comprising a score line connecting the proximal portion of the tip cap to the remainder of the tip cap.

5. The syringe of claim 3, wherein removal of the tip cap from the distal connector provides biofeedback to the user.

6. The syringe of claim 5, wherein the biofeedback includes an audible indication.

7. The syringe of claim 1, the tip cap further comprising a stem configured to engage the fluid aperture of the needle seal.

8. The syringe of claim 7, wherein the stem is constructed of an elastomeric material.

9. The syringe of claim 7, the stem further comprising at least one protrusion to secure the stem within the tip cap.

10. The syringe of claim 1, wherein the axial ledge is configured to abut the distal end of the barrel.

11. The syringe of claim 10, wherein the needle seal further comprises a protrusion configured to engage a window of the distal connector.

12. The syringe of claim 1, wherein the barrel is substantially straight from a first proximal end to a second distal end of the barrel.

13. The syringe of claim 1, wherein the plunger comprises a plunger member capable of engaging a retractable needle, a plunger housing, and a biasing member.

\* \* \* \* \*